United States Patent
Pagan

[19]

[11] Patent Number: 6,148,818
[45] Date of Patent: Nov. 21, 2000

[54] HELICALLY-REINFORCED TUBES

[75] Inventor: Eric Pagan, Hythe, United Kingdom

[73] Assignee: Smith Industries Public Limited Company, London, United Kingdom

[21] Appl. No.: 09/197,695

[22] Filed: Nov. 23, 1998

[30] Foreign Application Priority Data

Dec. 20, 1997 [GB] United Kingdom ................... 9726820

[51] Int. Cl.⁷ .................................................. A61M 16/00
[52] U.S. Cl. .................................. 128/207.15; 128/207.14
[58] Field of Search ........................ 128/207.14, 207.15, 128/911, 912; 604/524, 525, 526, 527; 138/144

[56] References Cited

U.S. PATENT DOCUMENTS

| | | | |
|---|---|---|---|
| 4,990,143 | 2/1991 | Sheridan | 604/282 |
| 5,695,482 | 12/1997 | Kaldany | 604/280 |
| 5,769,828 | 6/1998 | Jonkman | 604/280 |
| 5,827,242 | 10/1998 | Follmer et al. | 604/282 |
| 5,848,223 | 12/1998 | Carlson | 392/478 |
| 5,976,192 | 11/1999 | McIntyre et al. | 623/901 |

FOREIGN PATENT DOCUMENTS 0 769 631   9/1997   European Pat. Off. .

*Primary Examiner*—Aaron J. Lewis
*Assistant Examiner*—Teena Mitchell
*Attorney, Agent, or Firm*—Pollock, Vande Sande & Amernick, RLLP

[57] ABSTRACT

An endotracheal tube has a wall of PVC and a reinforcement filament of a harder plastics wound with a canted helical form so that adjacent turns of the filament slope at angles of 70° and 80° respectively in the plane of curvature of the tube.

11 Claims, 2 Drawing Sheets

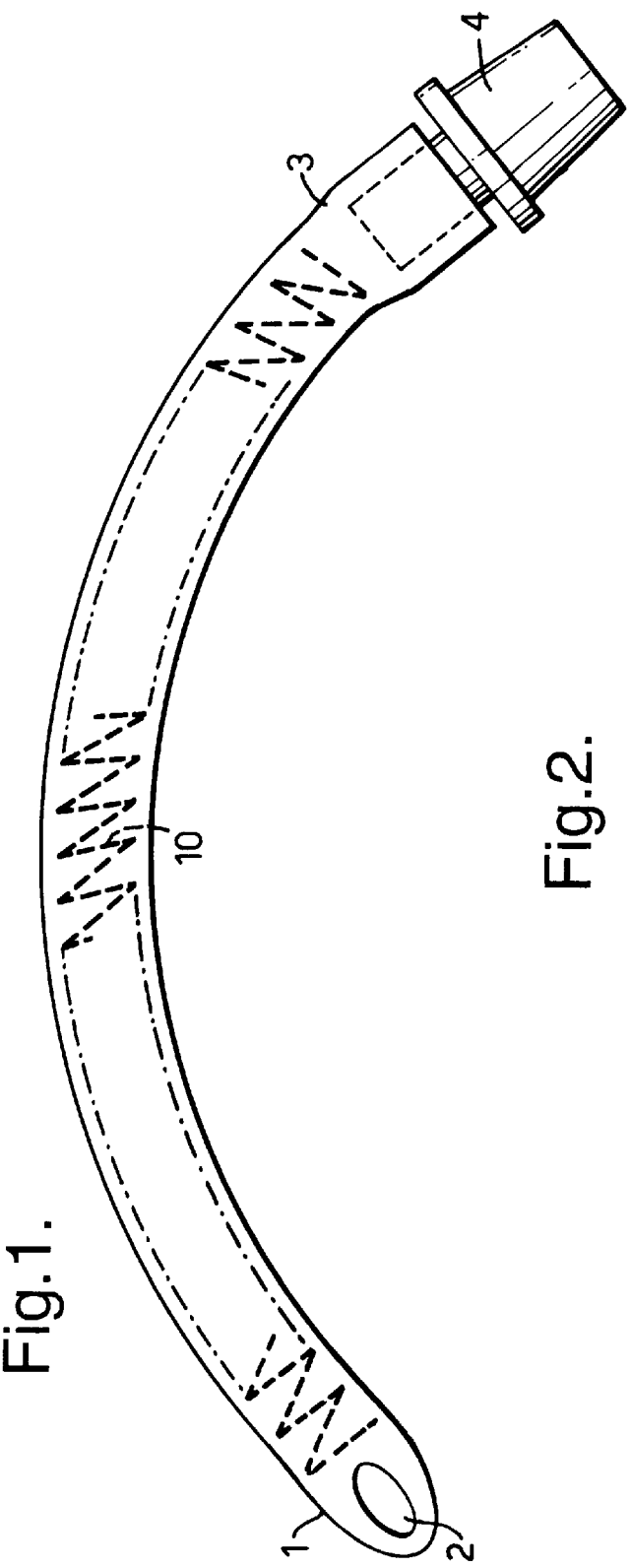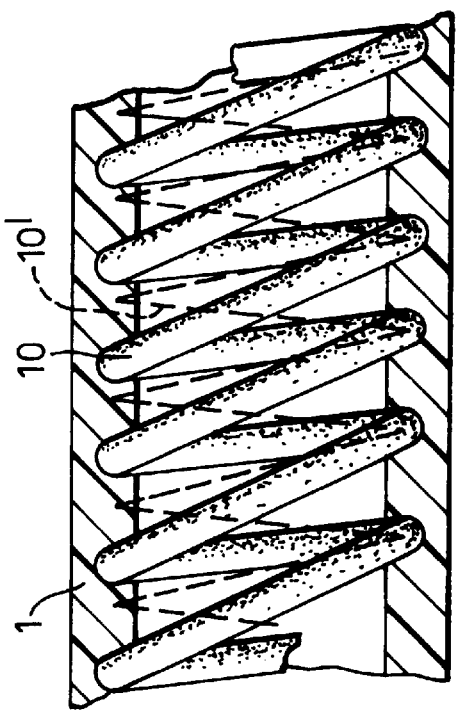

HELICALLY-REINFORCED TUBES

BACKGROUND OF THE INVENTION

This invention relates to tubes.

The invention is more particularly concerned with reinforced tubes, such as for medical or surgical use.

It is known for medical tubes to be reinforced by the inclusion of a helical reinforcing element. Such a helical reinforcing element helps to reduce the risk that the tube will be occluded by lateral forces and thereby enables the tube to have a thinner wall. Although such a reinforcing element increases crush resistance, compared with an unreinforced tube, the reinforced tube is still susceptible to crushing where a lateral force is exerted in a region narrower than the pitch of the reinforcing element. The tube is also still susceptible to kinking if the tube is bent around a small radius. Examples of reinforced tubes and their manufacture are described in GB2043201 and GB 2321095.

BRIEF SUMMARY OF THE INVENTION

It is an object of the present invention to provide an improved reinforced tube.

According to one aspect of the present invention there is provided a tube having first and second ends and a bore extending therethrough for the passage of fluid along the tube, the wall of the tube including a reinforcing element of a canted helix form.

Adjacent turns of the reinforcement element preferably slope in the same sense when viewed in elevation, such as at angles of 70° and 80° respectively. The tube is preferably curved along its length, the reinforcement element being canted in the plane of curvature of the tube. The reinforcement element may have a rectangular section. The wall of the tube may be of a first plastics, such as PVC, and the reinforcement element may be of a second plastics, such as polyester or nylon, different from the first plastics.

The tube may be a medico-surgical tube such as an endotracheal tube in which the first end is adapted for location in the trachea and the second end is adapted to extend from the mouth of the patient.

According to another aspect of the present invention there is provided a method of making a reinforced tube including the steps of forming a base tube, wrapping around the base tube a reinforcement filament in a canted helical fashion by longitudinally oscillating a shuttle as the filament is wrapped, and applying an outer layer of material over the filament.

The base tube is preferably made by extrusion.

An endotracheal tube according to the present invention, will now be described, by way of example, with reference to the accompanying drawings.

BRIEF DESCRIPTION OF THE DRAWINGS

FIG. 1 is a side elevation view of the tube;

FIG. 2 is a side elevation view of a part of the tube to a greater scale; and

DETAILED DESCRIPTION OF THE PREFERRED EMBODIMENT

Figure 3:
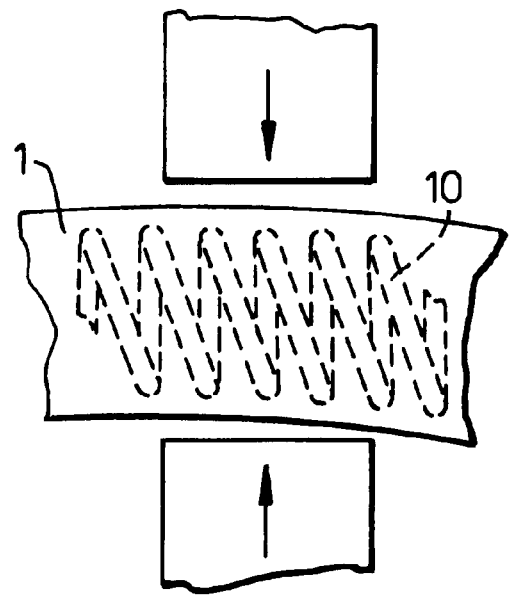
FIGS. 3 and 4 are side elevation views illustrating the effect of lateral forces applied to the tube.

With reference first to FIGS. 1 and 2, the endotracheal tube is of PVC, having a circular section with an external diameter between about 3 mm and 12 mm and a wall thickness between about 1 mm and 2.5 mm. The tube is typically about 300 mm long and is curved along its length with a radius of curvature of about 140 mm. The patient end 1 of the tube is bevelled to one side and has a Murphy eye 2 of conventional kind. The machine end 3 of the tube is fitted on a male fitting at one end of a connector 4, the other end of which is shaped to receive a mating coupling, such as connected to a patient ventilation circuit (not shown). The tube may have an inflatable cuff (not shown) close to its patient connected via an inflation lumen to a pilot balloon and connector. As so far described, the tube is conventional.

The tube includes a reinforcing element 10 extending from a location just rearwardly of the Murphy eye 2 to a location just forwardly of the machine end 3. The reinforcing element 10 is a polyester or nylon filament of rectangular section and about 0.25 mm thick wound into a canted helical path. Alternatively, the filament could have a circular section, although the rectangular section helps to reduce the wall thickness. The filament could be made of other materials, such as metal, polyester, nylon, Kevlar, polythene or polypropylene. The difference between a canted helix and a conventional helix is illustrated in FIG. 2 where the conventional helix is shown as a broken line 10' and the canted helix reinforcement filament 10 is shown as a full line. When viewed in elevation, a conventional helix has a sawtooth appearance, with opposite slopes of each tooth having equal and opposite angles. By contrast, a canted helix viewed in elevation, in the canted plane, has the two slopes of each tooth at different angles, one being steeper than the other. In effect, the canted helix is shaped as if one side of a conventional helix has been pushed longitudinally relative to the other side. In particular, in the present invention, the canted helix preferably has one slope canted in the same sense as the other slope at an angle close to vertical. Typically the slope angles of the two slopes might be 70° and 80°.

Figure 4:
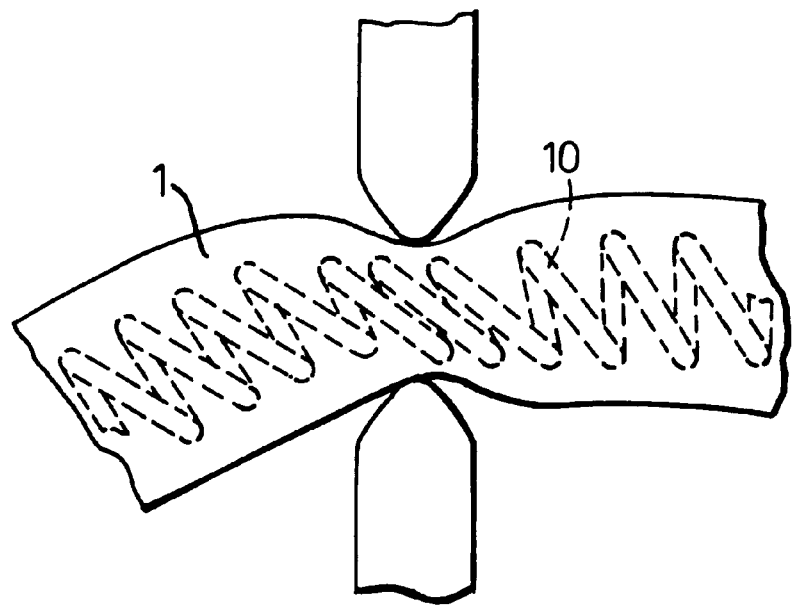

One advantage of the canted helix filament 10 can be seen when the effect of a lateral force on the tube is considered, as illustrated in FIGS. 3 and 4. If a lateral force were exerted over a length of the tube corresponding to several pitches of the reinforcement element, as shown in FIG. 3, a high force would be required to compress the tube because one slope of the element is almost vertical to the applied force. If the lateral force were, instead, exerted over a short length of the tube less than the pitch of the reinforcement element 10, as shown in FIG. 4, the effect would be to compress adjacent turns of the element towards one another. This has the effect of increasing the strength of the tube as the turns of the reinforcement element 10 are compressed closer towards one another. Such a localized force might be applied, for example, by teeth biting the tube. With a conventional helical reinforcement, a localized force of this kind would just separate the turns of the reinforcement. The canted reinforcement element 10 thereby gives the tube a greater resistance to crushing in the canted plane than a resistance of a tube with a conventional helical reinforcement element.

The reinforcement element 10 is canted in the plane of curvature of the tube, that is, the turns of the reinforcement element along the outside curvature of the tube are displaced longitudinally relative to the turns along the inside curvature. This ensures that the tube has the greatest resistance to crushing from lateral forces in the plane of curvature, which is where the majority of forces, such as from a teeth bite, will be experienced in an endotracheal tube.

When a tube is bent, there is a zone of compression on the inside of the bend and a zone of extension on the outside of the bend. With the tube of the present invention, there will be a greater number of turns of filament located in a compression/extension zone of given length, than in a conventional tube, so the energy produced on bending will be diverted more efficiently, with less risk of kinking. This reduced risk of kinking applies in all planes, but especially in the canted plane.

The tube is made by extruding a base tube of PVC and then winding the reinforcement filament around the outside of this in a canted helix fashion, by means of a shuttle that oscillates longitudinally as the filament is wrapped around the tube. The reinforcing filament is then retained on the base tube by a further extrusion such as of PVC, polyurethane, or TPE, or by a coating, such as applied by dip molding. Each tube may be made individually, with unreinforced portions left at opposite ends of the tube. Alternatively, a continuous length of tubing may be reinforced, which is then cut to length, the reinforcement element being removed from the end portions. In some tubes it may be unnecessary to have unreinforced end portions.

The invention is applicable to other tubes with a passage for conveying fluid. These may be medical tubes, such as, for example, cardiology catheters, urology catheters and enteral feeding catheters, or tubes for other applications such as industrial hoses.

What I claim is:

1. A tube comprising: a first end; a second end; a bore extending therethrough for the passage of fluid along the tube; and a wall with a reinforcing element of a canted helix form adapted to ensure resistance to crushing from lateral forces in the plane of curvature.

2. A tube according to claim 1, wherein adjacent turns of said reinforcement element slope in the same sense when viewed at right angles to the tube's longitudinal length.

3. A tube according to claim 1, wherein adjacent turns of said reinforcement element slope at angles of substantially 70° and 80° respectively.

4. A tube according to claim 1, wherein the tube is curved along its length, and wherein said reinforcement element is canted in the plane of curvature of the tube.

5. A tube according to claim 1, wherein said reinforcement element has a rectangular cross section.

6. A tube according to claim 1, wherein the wall of the tube is of a first plastics and said reinforcement element is of a second plastics different from the first plastics.

7. A tube according to claim 6, wherein the wall of the tube is of PVC and said reinforcement element is of polyester or nylon.

8. An endotracheal tube comprising: a first end adapted for location in the trachea; a second end adapted to extend from the mouth of the patient; a bore extending therethrough for the passage of gas along the tube; and a wall with a reinforcing element of a canted helix form; and wherein adjacent turns of said reinforcement slope in the same sense when viewed at right angles to the tube's longitudinal length.

9. A method of making a reinforced tube comprising the steps of: forming a base tube, wrapping around the base tube a reinforcement filament in a canted helical fashion by longitudinally oscillating a shuttle as the filament is wrapped, and applying an outer layer of material over the filament.

10. A method according to claim 9, wherein the base tube is made by extrusion.

11. A tube comprising: a first end; a second end; a bore extending therethrough for the passage of fluid along the tube; and a wall with a reinforcing element of a canted helix form; and wherein adjacent turns of said reinforcement element slope in the same sense when viewed at a right angle to the tube's longitudinal length with the two slopes of each tooth being at different angles.

* * * * *